United States Patent
Markel et al.

(10) Patent No.: US 8,598,322 B2
(45) Date of Patent: Dec. 3, 2013

(54) ANTI CEACAM1 ANTIBODIES AND METHODS OF USING SAME

(75) Inventors: Gal Markel, Tel Aviv (IL); Rona Ortenberg, Tel Aviv (IL)

(73) Assignees: Tel Hashomer Medical Research Infrastucture and Services Ltd., Ramat-Gan (IL); Ramot At Tel Aviv University Ltd., Tel Aviv (IL)

( * ) Notice: Subject to any disclaimer, the term of this patent is extended or adjusted under 35 U.S.C. 154(b) by 0 days.

(21) Appl. No.: 13/318,266

(22) PCT Filed: Apr. 29, 2010

(86) PCT No.: PCT/IL2010/000348
§ 371 (c)(1),
(2), (4) Date: Dec. 21, 2011

(87) PCT Pub. No.: WO2010/125571
PCT Pub. Date: Nov. 4, 2010

(65) Prior Publication Data
US 2012/0100158 A1 Apr. 26, 2012

Related U.S. Application Data

(60) Provisional application No. 61/213,040, filed on Apr. 30, 2009.

(51) Int. Cl.
*C07K 16/30* (2006.01)
*C07K 16/46* (2006.01)
*C12P 21/08* (2006.01)
*A61K 39/395* (2006.01)

(52) U.S. Cl.
USPC ............... 530/388.8; 530/387.1; 530/388.1; 530/391.1; 530/391.3; 530/391.7; 435/70.21; 424/130.1; 424/141.1; 424/155.1; 424/178.1; 424/181.1

(58) Field of Classification Search
None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 4,348,376 A | 9/1982 | Goldenberg | |
| 4,666,828 A | 5/1987 | Gusella | |
| 4,683,202 A | 7/1987 | Mullis | |
| 4,801,531 A | 1/1989 | Frossard | |
| 4,946,778 A | 8/1990 | Ladner et al. | |
| 5,192,659 A | 3/1993 | Simons | |
| 5,272,057 A | 12/1993 | Smulson | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg | |
| 2002/0028203 A1 | 3/2002 | Blumberg | |
| 2003/0022292 A1 | 1/2003 | Gray-Owen | |
| 2004/0047858 A1 | 3/2004 | Blumberg et al. | |
| 2004/0214184 A1 | 10/2004 | Skubitz | |
| 2005/0107324 A1 | 5/2005 | Bennett | |
| 2005/0169922 A1 | 8/2005 | Blumberg | |
| 2007/0071758 A1 | 3/2007 | Markel | |
| 2007/0110668 A1 | 5/2007 | Markel | |
| 2008/0102071 A1 | 5/2008 | Blumberg | |
| 2008/0108140 A1 | 5/2008 | Markel | |

FOREIGN PATENT DOCUMENTS

| | | |
|---|---|---|
| WO | 99/52552 A1 | 10/1999 |
| WO | 02/12535 A1 | 2/2002 |
| WO | 2007/063424 A2 | 6/2007 |
| WO | 20080029271 | 3/2008 |
| WO | 20090141679 | 11/2009 |

OTHER PUBLICATIONS

Balmana et al. Ann Oncol 2009; 20(supp 4):iv19-20.*
Nelson et al., Ann. Intern Med. 2009; 151:727-737.*
Kataja et al., Ann Oncol 2009; 20(sup 4): iv10-14.*
Brand et al., Anticancer Res. 2006; 26:463-70.*
Kammerer et al. J. Pathol 2004; 204:258-67.*
Laack et al., J Clin Oncol 2002; 20:4279-84.*
Thies et al., J Clin Oncol 2002; 20:2530-36.*
Gray-Owen & Blumberg, Nat. Rev. Immunol. 2006; 6:433-46.*
Besser, Michal J. et al., (2009) Minimally cultured or selected autologous tumor-infiltrating lymphocytes after a lympho-depleting chemotherapy regimen in metastatic melanoma patients. J Immunother 32(4):415-423.
Besser, Michal J. et al., (2010) Clinical responses in a phase II study using adoptive transfer of short-term cultured tumor infiltration lymphocytes in metastatic melanoma patients. Clin Cancer Res 16(9):2646-2655 Epub ahead of print Apr. 20, 2010.
Bird, Robert E. et al., (1988) Single-chain antigen-binding proteins. Science 242(4877):423-426.
Boerner, P. et al., (1991) Production of antigen-specific human monoclonal antibodies from in vitro-primed human splenocytes. J Immunol 147(1):86-95.
Fishwild, Dianne M. et al., (1996) High-avidity human IgG kappa monoclonal antibodies from a novel strain of minilocus transgenic mice. Nat Biotechnol 14(7):845-851.
Hoogenboom, Hennie R. et al., (1992) By-passing immunisation. Human antibodies from synthetic repertoires of germline VH gene segments rearranged in vitro. J Mol Biol 227(2):381-388.
Inbar, Dan et al., (1972) Localization of antibody-combining sites within the variable portions of heavy and light chains. Proc Natl Acad Sci USA 69(9):2659-2662.
Jones, Peter T. et al., (1986) Replacing the complementarity-determining regions in a human antibody with those from a mouse. Nature 321(6069):522-525.

(Continued)

*Primary Examiner* — Sheela J Huff
*Assistant Examiner* — Jessica H Roark
(74) *Attorney, Agent, or Firm* — Rothwell, Figg, Ernst & Manbeck, P.C.

(57) ABSTRACT

A hybridoma cell which has been deposited under ATCC Accession Number PTA-9974 is disclosed. Also provided are Antibodies and methods of using same.

18 Claims, 8 Drawing Sheets

(56) References Cited

OTHER PUBLICATIONS

Larrick, James W. et al., (1991) PCR amplification of antibody genes. Methods 2(2):106-110.
Lonberg, Nils et al., (1994) Antigen-specific human antibodies from mice comprising four distinct genetic modifications. Nature 368(6474):856-859.
Lonberg, Nils et al., (1995) Human antibodies from transgenic mice. Int Rev Immunol 13(1):65-93.
Marks, James D. et al., (1991) By-passing immunization. Human antibodies from V-gene libraries displayed on phage. J Mol Biol 222(3):581-597.
Marks, James D. et al., (1992) By-passing immunization: building high affinity human antibodies by chain shuffling. BioTechnology (NY) 10(7):779-783.
Morales, Victor M. et al., (1999) Regulation of human intestinal intraepithelial lymphocyte cytolytic function by biliary glycoprotein (CD66a). J Immunol 163(3):1363-1370.
Morrison, Sherie L. (1994) Immunology. Success in specification. Nature 368(6474):812-813.
Neuberger, Michael (1996) Generating high-avidity human Mabs in mice. Nat Biotechnol 14(7):826.
Pack, Peter et al., (1993) Improved bivalent miniantibodies, with identical avidity as whole antibodies, produced by high cell density fermentation of *Escherichia coli*. BioTechnology (NY) 11(11):1271-1277.
Porter, R. R. (1959) The hydrolysis of rabbit y-globulin and antibodies with crystalline papain. Biochem J 73:119-126.
Presta, Leonard G. (1992) Antibody Engineering. Curr Opin Struct Biol 2(4):593-596.
Riechmann, Lutz et al., (1988) Reshaping human antibodies for therapy. Nature 332(6162):323-327.
Roder, John C. et al., (1985) Recent advances in the ebv-hybridoma technique. In: Monoclonal antibodies and cancer therapy. Journal of Cellular Biochemistry Supplement: UCLA Symposia on Molecular & Cellular Biology 29 (9A):33-74 abstract #0106.
Verhoeyen, Martine et al., (1988) Reshaping human antibodies: grafting an antilysozyme activity. Science 239 (4847):1534-1536.
Whitlow, Marc and Filpula, David (1991) Single-chain Fv proteins and their fusion proteins. Methods 2(2):97-105.
ISR of PCT/IL10/00348 mailed Jul. 30, 2010.
Markel G et al., (2002) CD66a interactions between human melanoma and NK cells: a novel class I MHC-independent inhibitory mechanism of cytotoxicity. J Immunol 166(6): 2803-2810.
Markel G et al., (2002) Pivotal role of CEACAM1 protein in the inhibition of activated decidual lymphocyte functions. J Clin Invest 110(7): 943-953.
Markel G et al., (2004) Biological function of the soluble CEACAM1 protein and implications in TAP2-deficient patients. Eur J Immunol 34(8): 2138-2148.
Markel G et al., (2004) The critical role of residues 43R and 44Q of carcinoembryonic antigen cell adhesion molecules-1 in the protection from killing by human NK cells. J Immunol 173(6): 3732-3739.
Markel G et al., (2004) The mechanisms controlling NK cell autoreactivity in TAP2-deficient patients. Blood 103(5): 1770-1778.
Stern N et al., (2005) Carcinoembryonic antigen (CEA) inhibits NK killing via interaction with CEA-related cell adhesion molecule 1. J Immunol 174(11): 6692-6701.
Watt et al.,(2001) Homophilic adhesion of human CEACAM1 involves N-terminal domain interactions: structural analysis of the binding site. Blood 98 (5): 1469-1479.

\* cited by examiner

8,598,322 B2

ANTI CEACAM1 ANTIBODIES AND METHODS OF USING SAME

CROSS REFERENCE TO RELATED APPLICATIONS

This application is a 35 U.S.C. §371 National Phase Entry Application from PCT/IL2010/000348, filed Apr. 29, 2010, and designating the United States, which claims the benefit of U.S. Provisional Application No. 61/213,040, filed on Apr. 30, 2009, which are incorporated herein in their entireties.

FIELD AND BACKGROUND OF THE INVENTION

The present invention, in some embodiments thereof, relates to anti-CEACAM1 antibodies, hybridoma cells producing same and methods of using same.

The transmembrane protein CEACAM1 [also known as biliary glycoprotein (BGP), CD66a and C-CAM1] is a member of the carcinoembryonic antigen family (CEA) that also belongs to the immunoglobulin superfamily. CEACAM1 interacts with other known CD66 proteins, including CD66a, CD66c, and CD66e proteins. It is expressed on a wide spectrum of cells, ranging from epithelial cells to those of hemopoietic origin (e.g. immune cells).

Many different functions have been attributed to the CEACAM1 protein. It was shown that the CEACAM1 protein exhibits anti-proliferative properties in carcinomas of colon, prostate, as well as other types of cancer. Additional data support the central involvement of CEACAM1 in angiogenesis and metastasis. CEACAM1 also plays a role in the modulation of innate and adaptive immune responses. For example, CEACAM1 was shown to be an inhibitory receptor for activated T cells contained within the human intestinal epithelium [see WO99/52552 and Morales et al. J. Immunol. 163 (1999), 1363-1370]. Additional reports have indicated that CEACAM1 engagement either by TCR cross-linking with mAb or by Neisseria gonorrhoeae Opa proteins inhibits T cell activation and proliferation.

Melanoma is a malignancy of pigment-producing cells (melanocytes), responsible for 75% of skin cancer-related incidence worldwide, mainly due to extensive metastasis. Metastatic melanoma (MM) responds feebly to most anticancer regimens and overall survival mean for patients with MM is 8.5 months. CEACAM1 is rarely expressed by normal melanocytes, but frequently found on melanoma cells. CEACAM1 expression on primary cutaneous melanoma lesions strongly predicts the development of metastatic disease with poor prognosis. Moreover, increased CEACAM1 expression was observed on NK cells derived from some patients with metastatic melanoma compared with healthy donors.

WO2007/063424 and U.S. Patent Application No. 20070110668 disclose methods for regulating the immune system, and in particular methods for the regulation of a specific immune response, including the regulation of lymphocyte activity. These methods comprise both the negative and positive modulation of CEACAM1 protein function.

U.S. Patent Application No. 20070071758 discloses methods and compositions for the treatment and diagnosis of cancers. Specifically, U.S. Patent Application No. 20070071758 teaches methods and compositions for enhancing the efficacy of tumor-infiltrating lymphocyte (TIL) therapy in the treatment of cancer by negatively modulating the activity of the CEACAM1 protein, such as for example, by using an immunoglobulin specific for CEACAM1.

U.S. Patent Application No. 20080108140 discloses methods of modulating specific immune responses to create a protective immunity in the treatment of autoimmune diseases and diseases requiring the transplantation of tissue. In particular, U.S. Patent Application No. 20080108140 relates to the suppression of immune responses in a targeted fashion, by increasing the functional concentration of the CEACAM1 protein in the target tissue.

U.S. Patent Application No. 20040047858 discloses specific antibodies (i.e. 34B1, 26H7 and 5F4) which are capable of modulating T cell activity via CEACAM1 and uses thereof such as in treating immune response related diseases (e.g. graft versus host disease, autoimmune diseases, cancers etc.).

U.S. Patent Application Nos. 20020028203, 20050169922 and 20080102071 disclose compositions which bind T cell inhibitory receptor molecules and modulate (i.e. enhance or suppress) T cell activity (e.g. cytotoxicity and proliferation), such as biliary glycoprotein binding agents, and methods of using such compositions such as for treatment of diseases (e.g. an autoimmune disease, immunodeficiency, cancer etc.).

Other related art:

5F4 mAb: Regulation of human intestinal intraepithelial lymphocyte cytolytic function by biliary glycoprotein (CD66a) [Morales V M et al., J Immunol. (1999) 163(3): 1363-70].

GM8G5 and 29H2—both available commercially from Abcam Inc. abcamdotcomdotportal.

SUMMARY OF THE INVENTION

According to an aspect of some embodiments of the present invention there is provided a hybridoma cell which has been deposited under ATCC Accession Number PTA-9974.

According to an aspect of some embodiments of the present invention there is provided an isolated antibody or antibody fragment comprising an antigen recognition domain having the CDR sequences and orientation of the antibody produced from the hybridoma cell.

According to an aspect of some embodiments of the present invention there is provided a method of immunomodulation, the method comprising contacting a CEACAM1-expressing lymphocyte with the antibody or antibody fragment.

According to an aspect of some embodiments of the present invention there is provided a method of inhibiting migration or proliferation of a CEACAM1 expressing tumor cell, the method comprising contacting the CEACAM1 expressing tumor cell with the antibody or antibody fragment, thereby inhibiting migration or proliferation of a CEACAM1 expressing tumor cell.

According to an aspect of some embodiments of the present invention there is provided a method for diagnosing a cancer in a subject in need thereof, the method comprising contacting a biological sample derived from the subject with the antibody or antibody fragment, wherein a complex formation beyond a predetermined threshold is indicative of the cancer in the subject.

According to an aspect of some embodiments of the present invention there is provided a method of treating cancer, the method comprising administering to a subject in need thereof a therapeutically effective amount of the antibody or antibody fragment, thereby treating the cancer in the subject.

According to an aspect of some embodiments of the present invention there is provided a method of inhibiting CEACAM1 homotypic or heterotypic protein-protein interaction, the method comprising contacting a CEACAM1-expressing lymphocyte with the antibody or antibody fragment, thereby inhibiting CEACAM1 homotypic or heterotypic protein-protein interaction.

According to an aspect of some embodiments of the present invention there is provided a pharmaceutical composition comprising as an active ingredient the antibody or antibody fragment.

According to some embodiments of the invention, the isolated antibody or antibody fragment is attached to a cytotoxic moiety.

According to some embodiments of the invention, the cytotoxic moiety comprises a cytotoxin, a chemokine, a chemotherapy, a pro-apoptotic, an interferon, a radioactive moiety, or combinations thereof.

According to some embodiments of the invention, the isolated antibody or antibody fragment is attached to an identifiable moiety.

According to some embodiments of the invention, cells of the cancer are characterized by over expression of CEACAM1 as compared to unaffected cells.

According to some embodiments of the invention, the method of treating cancer further comprises administering to the subject lymphocytes.

According to some embodiments of the invention, the lymphocytes comprise T cells or NK cells.

According to some embodiments of the invention, the CEACAM1-expressing lymphocyte is a Tumor Infiltrating Lymphocyte or NK cell.

According to some embodiments of the invention, the CEACAM1-expressing lymphocyte is a cytotoxic T cell.

According to some embodiments of the invention, the tumor cell comprises a melanoma tumor cell.

According to some embodiments of the invention, the cancer is melanoma.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 6A: simultaneous injections of the antibody (0.5 mg/mouse intraperitoneally) and inoculation of cancer cells (5,000,000 cells subcutaneously); FIG. 6B: treatment of tumors generated in SCID mice (tumor volume of 75 $mm^3$) by injections of MRG1 antibody (as indicated above).

DESCRIPTION OF EMBODIMENTS OF THE INVENTION

Figure 1A:
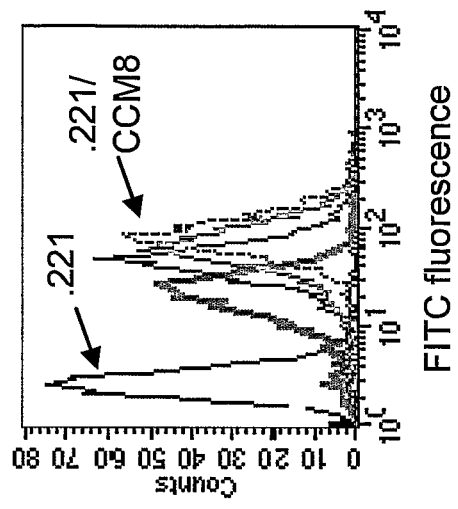
FIGS. 1A-B depict the specificity of MRG1 mAb. 721.221 parental B cells stably transfected with CEACAM1 (green), CEACAM5 (red), CEACAM6 (purple), CEACAM8 (blue) or mock (black), were subjected to FACS analysis using the different anti-human CEACAM antibodies: MRG1 mAb (FIG. 1A) and Kat4c mAb (FIG. 1B).

The present invention, in some embodiments thereof, relates to anti CEACAM1 monoclonal antibody and hybridoma cells producing same as well as methods of using the antibody in immunomodulation and cancer treatment.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventor has produced through laborious experimentation and screening a monoclonal antibody selective for CEACAM1. This antibody was shown to be superior to other anti CEACAM1 monoclonal antibodies as demonstrated by functional blocking assays.

As is illustrated herein below, the MRG1 antibody produced according to the present teachings, is selective to CEACAM1 and does not cross react with other members of the CEACAM family (i.e., CEACAM 5, 6 and 8, see Example 2). The antibody inhibits CEACAM1 homophilic interactions, as determined by co-incubation of immune effector cells and target melanoma cells and assaying IL-2 secretion and cell lysis (see Example 3). In addition the antibody was shown effective in inhibiting melanoma cells invasion and proliferation. Finally, in vivo administration of the antibody either alone or in combination with reactive lymphocytes was shown effective in inhibiting growth of melanoma tumors. Altogether, the present teachings suggest that the MRG1 antibody, fragments and derivatives can be used as an effective tool for immunomodulation and cancer treatment.

Thus according to an aspect of the invention there is provided a hybridoma cell which has been deposited at the American Type Culture Collection (ATCC), 10801 University Blvd., Manassas, Va., 20110-2209, United States of America, under ATCC Accession Number PTA-9974, on Apr. 29, 2009.

According to a further aspect of the invention there is provided an isolated antibody or antibody fragment comprising an antigen recognition domain having the CDR segments and orientation of the antibody produced from the hybridoma cell, described above.

The antibody of the present teachings is capable of binding CEACAM1 with a minimal affinity of $10^{-6}$, $10^{-7}$, $10^{-8}$, $10^{-9}$ M.

As used herein the term "CEACAM1" refers to the protein product of the CEACAM1 gene e.g., NP_001020083.1, NP_001703.2.

The term "antibody" as used in this invention includes intact molecules as well as functional fragments thereof, such as Fab, F(ab')2, and Fv that are capable of binding to macrophages. According to an exemplary embodiment the antibody is a monoclonal antibody such as termed herein, MRG1. Functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

As indicated above, the antibody of the present invention has the same complementarity determining regions (CDR) orientation as that of the antibody produced by hybridoma cell, having the deposit details as described above. That is CDR1, CDR2, CDR3 are placed in the same orientation on $V_H$ and $V_L$ chains.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946, 778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)]. According to some embodiments of the present invention, the CDRs can be implemented in any form of an antibody such as by the use of recombinant DNA technology.

Humanized forms of non-human (e.g., murine) antibodies are chimeric molecules of immunoglobulins, immunoglobulin chains or fragments thereof (such as Fv, Fab, Fab', F(ab') .sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to some embodiments of the invention, the antibody is attached to a cytotoxic moiety.

According to some embodiments of the invention, the antibody is attached to an identifiable moiety.

The identifiable moiety can be a member of a binding pair, which is identifiable via its interaction with an additional member of the binding pair and a label which is directly visualized. In one example, the member of the binding pair is an antigen which is identified by a corresponding labeled antibody. In one example, the label is a fluorescent protein or an enzyme producing a colorimetric reaction.

The following Table 1 provides examples of sequences of identifiable moieties.

TABLE 1

| Identifiable Moiety | Amino Acid sequence (Genebank Accession No.) | Nucleic Acid sequence (Genebank Accession No.) |
|---|---|---|
| Green Fluorescent protein | AAL33912 | AF435427 |
| Alkaline phosphatase | AAK73766 | AY042185 |
| Peroxidase | NP_568674 | NM_124071 |
| Histidine tag | AAK09208 | AF329457 |
| Myc tag | AF329457 | AF329457 |
| Biotin lygase tag | NP_561589 | NC_003366 |
| orange fluorescent protein | AAL33917 | AF435432 |
| Beta galactosidase | NM_125776 | NM_125776 |
| Fluorescein isothiocyanate | AAF22695 | AF098239 |
| Streptavidin | S11540 | S11540 |

The cytotoxic or therapeutic moiety can be, for example, a cytotoxic moiety, a toxic moiety, a cytokine moiety, a bi-specific antibody moiety, a cytotoxin, a chemokine, a chemotherapy, a pro-apoptotic, interferon, a radioactive moiety, or combinations thereof, examples of which are provided infra.

The following Table 2 provides examples of sequences of therapeutic moieties.

TABLE 2

| Therapeutic moiety | Amino acid sequence (GenBank Accession No.) | Nucleic acid sequence (GenBank Accession No.) |
|---|---|---|
| [i Pseudomonas [l exotoxin | ABU63124 | EU090068 |
| Diphtheria toxin | AAV70486 | AY820132.1 |
| interleukin 2 | CAA00227 | A02159 |
| CD3 | P07766 | X03884 |
| CD16 | NP_000560.5 | NM_000569.6 |
| interleukin 4 | NP_000580.1 | NM_000589.2 |
| HLA-A2 | P01892 | K02883 |
| interleukin 10 | P22301 | M57627 |
| Ricin toxin | EEF27734 | EQ975183 |

It will be appreciated that such fusions can be effected using chemical conjugation or by recombinant DNA technology.

The antibody of the present invention can decrease the inhibitory CEACAM1 homophilic (or homotypic) or heterotypic interactions to thereby augment the activity of lymphocytes. CEACAM1 homophilic interactions occur through the N-domain. Several amino acids are crucial for this interaction, including R43, Q44, D64 and R82. The interaction causes phosphorylation of a cytoplasmic tyrosine residue that recruits SHP-1 phosphatase. This initiates an inhibitory cascade within the lymphocytes, which targets proximal mediators, such as ZAP70.

Thus, the antibody of the present invention can be used to block CEACAM1 on either or both immune effector cells (CEACAM1 expressing lymphocytes e.g., tumor infiltrating cells, T cells or NK cells) and target cells (e.g., CEACAM1 expressing pathological cells such as cancer cells). Examples of cancer cells which are candidates for this therapy include, but are not limited to, melanoma, lung, thyroid, breast, colon, prostate, hepatic, bladder, renal, cervical, pancreatic, leukemia, lymphoma, myeloid, ovarian, uterus, sarcoma, biliary, or endometrial cells.

The present invention also contemplates isolated antibodies or antibody fragments-that compete for binding to CEACAM1 with the antibodies produced by the above-described hybridoma cell. Those antibodies may be humanized, xenogeneic, or chimeric antibodies (as described in detail above) being suitable for e.g. therapeutic applications. An antibody fragment of the antibody can be, for example, a single chain Fv fragment, an F(ab') fragment, an F(ab) fragment, and an F (ab')2 fragment. Thus, according to a further aspect of the invention there is provided a method of rendering a CEACAM1 expressing tumor cell susceptible to immunomodulation. The method comprising contacting the CEACAM1 expressing tumor cell (e.g., melanoma, lung, thyroid, breast, colon, prostate, hepatic, bladder, renal, cervical, pancreatic, leukemia, lymphoma, myeloid, ovarian, uterus, sarcoma, biliary or endometrial cell) with the antibody or antibody fragment described above, thereby rendering the CEACAM1 expressing tumor cell susceptible to immunomodulation.

As used herein "immunomodulation" refers to lymphocyte dependent immunomodulation (e.g., by NK cells or tumor infiltrating lymphocytes).

Additionally or alternatively, the present invention also envisages a method of immunomodulation (e.g., inhibiting CEACAM1 homotypic or heterotypic protein-protein interaction), by contacting a CEACAM1-expressing lymphocyte with the antibody or antibody fragment described herein.

The methods of the present teachings can be effected in-vitro, ex-vivo (e.g., used in T cell based adoptive immunotherapy) or in-vivo.

As mentioned, antibodies of some embodiments of the invention can have anti cancer activity which is independent from its immunomodulatory activity described above.

Thus, the present teachings further provide for a method of inhibiting migration or proliferation of a CEACAM1 expressing tumor cell, the method comprising contacting the CEACAM1 expressing tumor cell with the antibody or antibody fragment described herein, thereby inhibiting migration or proliferation of a CEACAM1 expressing tumor cell.

As used herein "inhibiting" refers to at least 5%, 10%, 20%, 30%, 40%, 50%, 60%, 70%, 80% 100% inhibition in proliferation or migration which can be assayed using methods which are well known in the art (see examples section below).

Antibodies of the present invention can be effectively used for the treatment of cancer.

Thus according to a further aspect there is provided a method of treating cancer, the method comprising administering to a subject in need thereof a therapeutically effective amount of the antibody or antibody fragment described herein, thereby treating the cancer in the subject. Examples of cancer which can be diagnosed or treated according to the present teachings include, but are not limited to, melanoma, sarcoma, lung cancer, cancer of the thyroid, breast cancer, colon cancer, prostate cancer, hepatic cancer, bladder cancer, renal cancer, cervical cancer, pancreatic cancer, leukemia, lymphoma, myeloid cell related cancer, ovarian cancer, uterus cancer, biliary cancer or endometrial cancer.

According to a specific embodiment of the present invention, the cancer is melanoma.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

In order to enhance treatment (e.g. cancer treatment), lymphocytes such as T cells (e.g. Tumor Infiltrating Lymphocytes) or NK cells may be administered to the subject prior to, concomitantly with or following administration of the antibody or antibody fragment of the present invention. Accordingly, lymphocytes may be obtained from the subject (e.g. from the peripheral blood or from the tumor of same) or from a donor (an allogeneic or a syngeneic lymphocyte donor), treated by ex-vivo expansion methods as to obtained viable lymphocytes [e.g. by growth on irradiated feeder layer supplemented with IL-2, as previously described in Besser M J et al., Clin Cancer Res (Epub ahead of print) 2010 May 1 and in Besser M J et al., Journal of Immunotherapy (Epub ahead of print) 2009 Apr 1, fully incorporated herein by reference] and administered to the subject.

It will be appreciated that the subject may be treated by any other anti-cancer treatment (e.g. chemotherapy, radiation therapy, etc.) prior to administration of the antibody or antibody fragment or prior to administration of the lymphocytes.

The antibody of the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion);

molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide antibody levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Therapeutic efficacy can be further validated in correlative animal models which are well known in the art. Human xenografts in immunodeficient mice. Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Aside from therapeutic applications, antibodies of the present invention can also be used in diagnostic applications.

Thus, according to a further aspect there is provided a method for diagnosing a cancer in a subject in need thereof, the method comprising contacting a biological sample derived from the subject (in-vivo or ex-vivo) with the antibody or antibody fragment described herein, wherein a complex formation beyond a predetermined threshold is indicative of the cancer in the subject. According to some embodiments, cells of the cancer are characterized by over expression of CEACAM1 as compared to unaffected cells.

As mentioned, the method of the invention is effected under conditions sufficient to form an immunocomplex; such conditions (e.g., appropriate concentrations, buffers, temperatures, reaction times) as well as methods to optimize such conditions are known to those skilled in the art, and examples are disclosed herein. As used herein the phrase "immunocomplex" refers to a complex which comprises the antibody of the invention and the CEACAM1.

Determining a presence or level of the immunocomplex of the invention may be direct or by detecting an identifiable (detectable) moiety which may be attached to the antibody.

The level of the immunocomplex in the tested cell (e.g., a cell of a subject in need thereof) is compared to a predetermined threshold. It will be appreciated that the antibody of the present invention can also be used to measure the amount of serum soluble CEACAM1. Regardless, the threshold may be determined based on a known reference level and/or a level in a control cell or serum. The control cell can be obtained from a control, healthy subject (e.g., a subject not suffering from the cancer) or from the same subject prior to disease initiation or following treatment. According to some embodiments of the invention, the control subject is of the same species e.g. human, preferably matched with the same age, weight, sex etc. as the subject in need thereof.

As used herein the term "diagnosing" refers to determining presence or absence of a pathology, classifying a pathology or a symptom, determining a severity of the pathology, monitoring pathology progression, forecasting an outcome of a pathology and/or prospects of recovery.

To facilitate diagnosis, the above teachings can be combined with other methods of diagnosing cancer which are well known in the art include but are not limited to imaging, molecular tests and surgical biopsies.

Once the diagnosis is established the subject is informed of the diagnosis and suitable treatments may be initiated.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Monoclonal Antibodies

Generation of MRG1 monoclonal antibodies

A monoclonal antibody that effectively blocks the CEACAM1 homophilic interactions in vitro at nanomolar concentrations was generated. Briefly, mice were immunized 3 times, at 2 week intervals, with 5 micrograms of recombinant human CEACAM1 (entire protein, commercially available from R&D Systems). Splenocytes were harvested and fused with SP2/0 cells, to generate a hybridoma library.

The hybridoma producing the CEACAM1-blocking antibody (MRG1 mAb) was re-cloned several times to yield a stable clone.

Other monoclonal antibodies

Kat4c mAb and rabbit polyclonal anti-CEACAM were purchased from DAKO (Glostrup, Denmark).

Example 2

Specificity of the Anti CEACAM1 mAb

MATERIALS AND EXPERIMENTAL PROCEDURES

Generation of CEACAM expressing cells

CEACAM-negative 721.221 human cells (parental B cells) were stably transfected with CEACAM1, CEACAM5, CEACAM6 or CEACAM8 by electroporation and selection with G418.

The murine thymoma BW parental cells (cells that lack TCR alpha and beta chains, yet retain full secretion machinery of IL-2) were transfected with a chimeric molecule comprising the extracellular portion of human CEACAM1 fused to the transmembrane and cytosolic tail of murine zeta chain. Transfection was performed by electroporation and selection with G418.

Antibody screening by FACS

Hybridomas were screened for CEACAM1 binding activity by flow cytometry as follows:

(a) 50,000 transfected CEACAM cells were placed in 96-U shaped wells.

(b) The cells were washed with cold FACS buffer (PBS, BSA 0.5%, Azide 0.05%).

(c) The cells were incubated with the staining mAb (MRG1 or Kat4c): 0.1 micrograms of mAb per 100 microliters, for 30 minutes, on ice.

(d) The cells were centrifuged, supernatants were removed and the cells were resuspended in 100 microliter FITC-conjugated goat anti mouse antibodies (Jackson Immunoresearch) at a dilution of 1:200.

(e) After 30 minute incubation (on ice in dark conditions), the cells were centrifuged, washed and re-suspended in FACS buffer.

(f) Cells were analyzed using a FACScalibur and CellQuest software.

Results

Figure 1B:
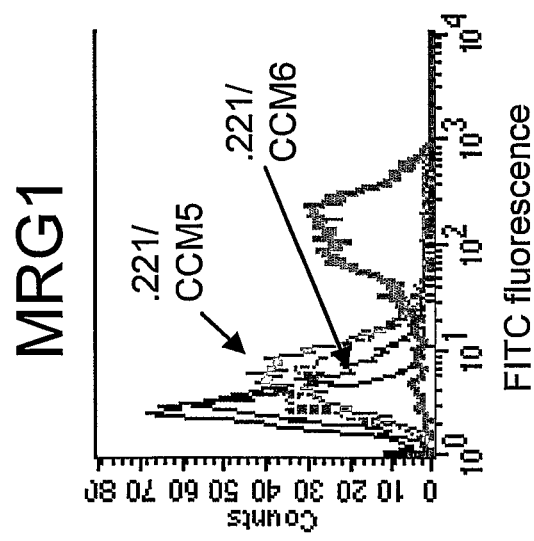

As 721.221 parental cells do not express any of the CEACAM proteins, these cells were stably transfected with CEACAM1, CEACAM5, CEACAM6 or CEACAM8 in order to test the specificity of the CEACAM1 monoclonal antibodies (mAbs). The hybridomas were then screened for CEACAM1 binding activity by flow cytometry. As shown in FIG. 1A, the MRG1 mAb generated according to the present teachings is specific to human CEACAM1. It has an insignificant cross-reactivity to CEACAM5 and no binding to CEACAM6 or CEACAM8. FIG. 1B shows that all transfectants expressed CEACAM molecules, with CEACAM1 being the lowest, which emphasizes the specificity pattern of MRG1.

Example 3

The mAb is Capable of Inhibiting CEACAM1 Homophilic Binding

Materials and Experimental Procedures

Antibody screening by ELISA

CEACAM1 blocking activity was tested using a BW functional system. The BW functional system comprises a mouse cell line (BW) stably transfected with a chimeric molecule comprising the extracellular domain of human CEACAM1 fused to mouse zeta chain (BW/CEACAM1-zeta, see Example 2, above). Co-incubation of the BW/CEACAM1-zeta cells with other CEACAM1-positive cells resulted in the secretion of measurable concentrations of mouse IL-2.

Thus, BW/CEACAM1-zeta (effector cells) or 221/CEACAM1 (target cells) were each pre-incubated separately with 10-40 ng/ml MRG1 mAb. Following one hour incubation on ice, the reciprocal cells (221/CEACAM1 or BW/CEACAM1) were added and the secretion of mouse IL-2 was measured by sandwich ELISA (R&D systems).

Cytotoxicity assay

Cytotoxicity assays testing the killing of various melanoma lines by tumor infiltrating lymphocytes was performed in the presence or absence of 1 μg/ml MRG1 mAb. CEACAM1$^{High}$ 526mel1, 624mel and CEACAM1$^{dim}$ 09mel melanoma cells were used as target cells. TIL014 cells were used as effector cells at an E:T ratio of 10:1. Following one hour incubation with the MRG1 mAb on ice, the reciprocal cells were added and co-incubated for 5 hours at 37° C. Target cells were pre-labeled with a green fluorescent dye (CFSE) and specific lysis was determined by Propidium Iodide (PI) co-staining in flow cytometry. Spontaneous death was subtracted.

Results

Figure 2:
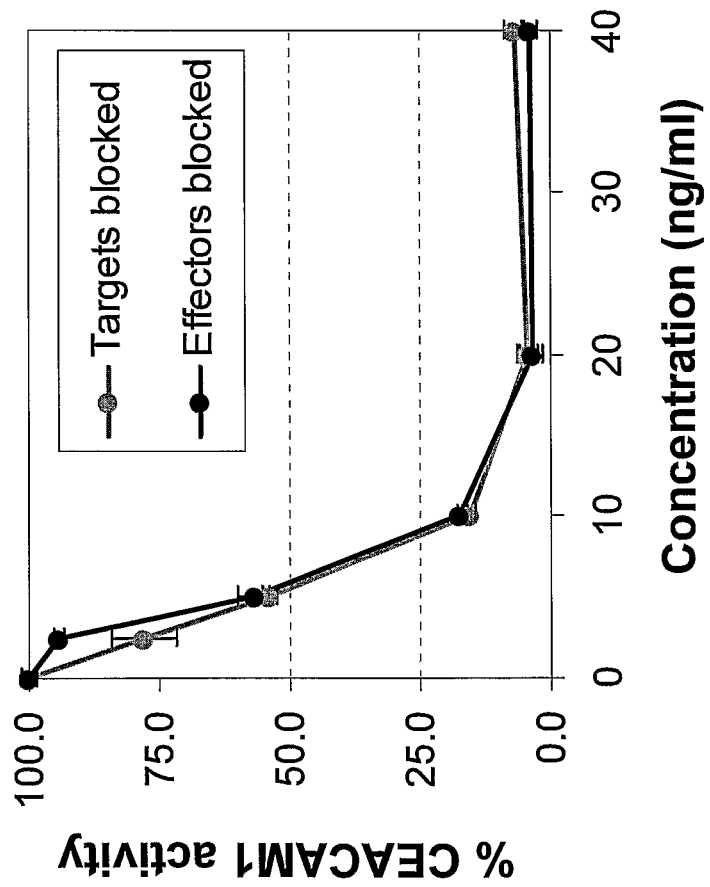
FIG. 2 depicts a dose-dependent inhibition of CEACAM1 homophilic interactions by the anti-CEACAM1 mAb MRG1. Anti-CEACAM1 mAb was added to either BW/CEACAM1 (effector cells) or 221/CEACAM1 (target cells) in various concentrations. Following one hour incubation on ice, the reciprocal cells (221/CEACAM1 or BW/CEACAM1) were added and the secretion of mouse IL-2 was measured by ELISA. 100% is defined as the activity in the absence of any antibody. The results of one representative experiment out of four are presented, each performed in triplicates.

The capability of the purified MRG1 mAb to inhibit CEACAM1 homophilic binding was verified. As shown in FIG. 2, the purified mAb MRG1 showed a dose-dependant inhibition of CEACAM1 homophilic binding. At a concentration of 10 ng/ml, the mAb efficiently reduced CEACAM1 interactions, effectively reaching a plateau at a concentration of 20 ng/ml. Importantly, the two experimental settings i.e. the addition of MRG1 mAb to the effector cells, BW/CEACAM1-zeta, or to the target cells, 221/CEACAM1, showed similar results (secretion of the mouse IL-2 was effectively blocked).

Figure 3:
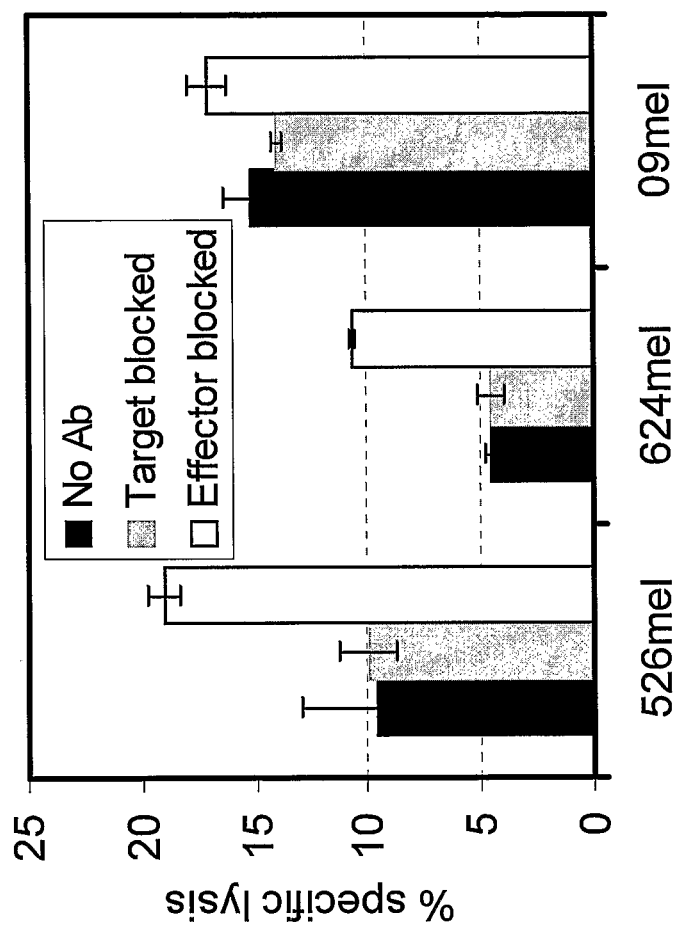
FIG. 3 depicts abolishment of CEACAM1-inhibitory function. MRG1 mAb was pre-incubated with target cells (depicted in grey) or with effector cells (depicted in white). Cells incubated without the addition of the mAb are depicted in black. The melanoma lines indicated (526mel, 624mel or 09mel) were used as target cells. TIL014 cells were used as effector cells in an E:T ratio of 10:1. Following one hour incubation on ice, the reciprocal cells were added and co-incubated for 5 hours at 37° C. Target cells were pre-labeled with green fluorescent dye (CFSE) and specific lysis was determined by Propidium Iodide (PI) co-staining in flow cytometry. Spontaneous death was subtracted. Assay was performed in triplicates.

The blocking effect of MRG1 mAb was further demonstrated in cytotoxicity assays. As shown if FIG. 3, killing of the CEACAM1$^{High}$ 526mel and 624mel cells was enhanced by incubation of the antibody with effector cells (but not on target cells). The killing of the CEACAM1$^{dim}$ 09mel cells was unaffected by the presence of MRG1 mAb (FIG. 3).

Example 4

Anti CEACAM1 mAb Inhibits Cancer Cell Migration and Proliferation

Materials and Experimental Procedures

Invasion assay

The blocking effect of the antibodies was tested in an invasion assay. Briefly, melanoma cells (08mel or 09mel) were pre-incubated in the presence or absence of 1 μg/ml MRG1 mAb and then tested by Matrigel invasion assays. Invasion was allowed for 24 hours and the amount of invading cells was quantified with standardized XTT.

Net proliferation assay

CEACAM1$^{High}$ 526mel cells were seeded on day 0 in 48-well plates (2,500 cells per well). On seeding, MRG1 was added in 3 different concentrations (0.5, 1, or 3 μg/ml), or not added at all. Total viable cells were counted 2 days or 5 days after seeding. Proliferation was determined with standardized XTT and by direct cell counting.

Results

Figure 4:
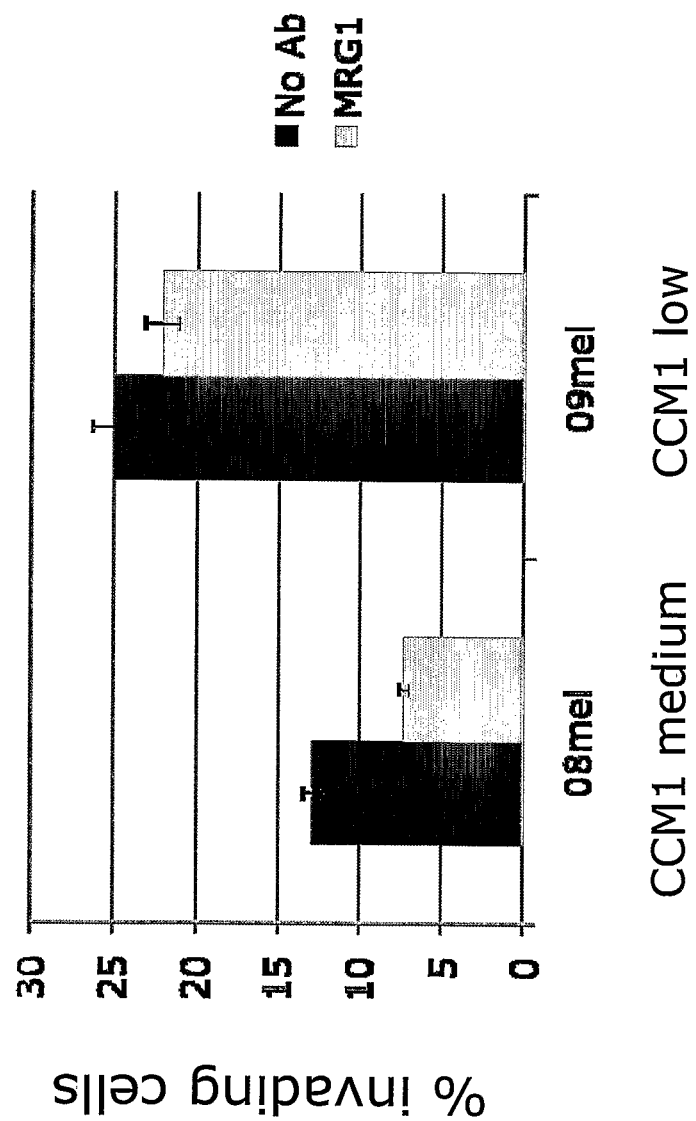
FIG. 4 depicts blocking of melanoma invasion by MRG1 mAbs. Melanoma cells (08mel or 09mel) were pre-incubated in the absence or presence of 1 μg/ml MRG1 mAb and then tested by Matrigel invasion assays. Invasion was allowed for 24 hours and the amount of invading cells was quantified with standardized XTT.

As shown in FIG. 4, MRG1 blocked the invasion of CEACAM1-positive 08mel cells (CEACAM1 expression level was medium, i.e. median fluorescence intensity of CEACAM1 expression was 50) and had little or no effect on CEACAM1dim 09mel cells (CEACAM1 expression level was low, i.e. median fluorescence intensity of CEACAM1 expression was 15).

Figure 5:
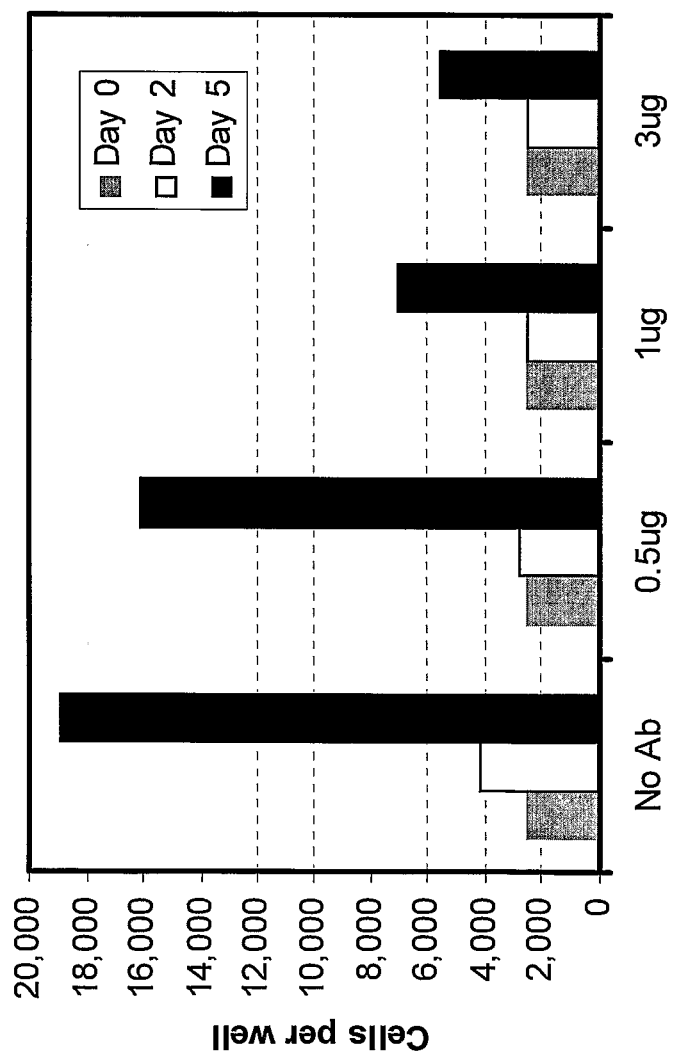
FIG. 5 depicts blocking of net proliferation of melanoma cells by MRG1 mAbs. 526mel melanoma cells were incubated with the indicated doses (0.5 μg, 1 μg or 3 μg) of MRG1 mAbs and proliferation was monitored 2 days or 5 days following treatment.

MRG1 was also tested in net proliferation assays. A dose-dependent inhibition in net proliferation of 526mel cells was observed (FIG. 5). Following 5 days of treatment, proliferation was reduced by more than 60% (with 3 μg MRG1 mAb).

Example 5

MRG1 Inhibits Cancer Cell Growth in Animal Experimental Models

Materials and Experimental Procedures

Melanoma xenograft models $5 \times 10^6$ CEACAM1$^+$ human melanoma cells were injected subcutaneously to the flank of 7 week old SCID-NOD mice.

Tumor masses formed in 100% of the mice within 14-17 days and continued to grow. Tumor dimensions were monitored non-invasively with a caliper 3 times a week and volume approximation was calculated as (d1×d2×d3/2).

Administration of MRG1 was performed by injection of 0.5 mg antibody diluted in 0.5 ml sterile PBS intraperitoneally. Injection of PBS served as control.

Administration of reactive human anti-melanoma lymphocytes was performed by intravenous injection into the tail vein of 20×10$^6$ cells diluted in 200 µl of sterile PBS.

Results

Figure 6A:
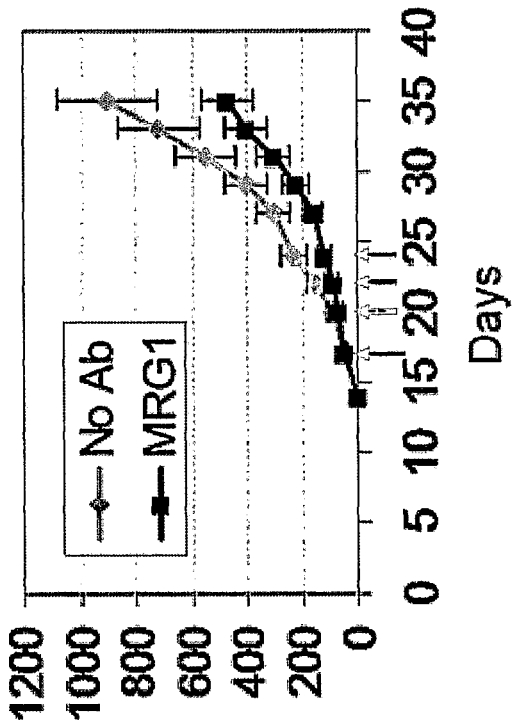
FIGS. 6A-B depict inhibition of human tumor growth in vivo in SCID mice by systemic injections of MRG1 as compared to PBS. Experiments were performed in two setups as follows.
Figure 6B:
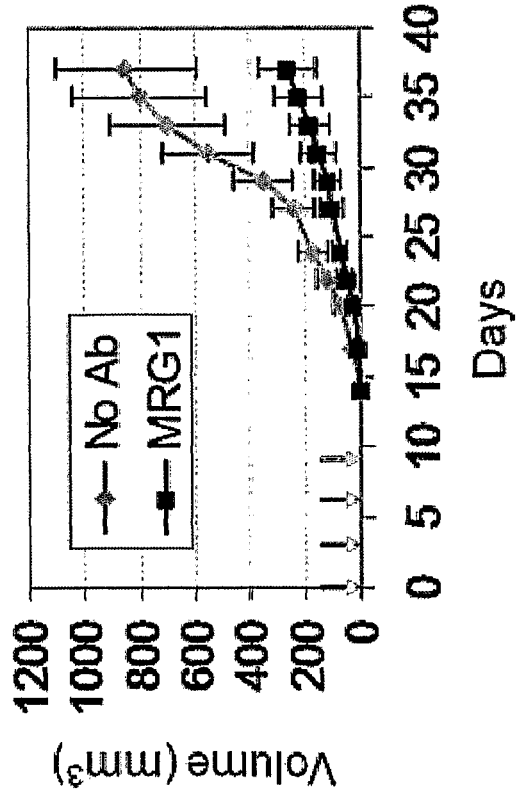

In line with the blocking functions demonstrated above, administration of MRG1 antibody inhibited tumor growth. This effect was evident when the antibody was administered at the time of tumor cell inoculation (FIG. 6A, "Prevention setup") or after a measurable tumor mass was already formed (FIG. 6B, "Treatment setup"). These effects were evident after 4 injections within 8 days, followed by non-invasive monitoring (see arrows in FIG. 6). It should be noted that this effect was independent of any immunomodulating effect, as SCID-NOD mice are immunodeficient.

Figure 7:
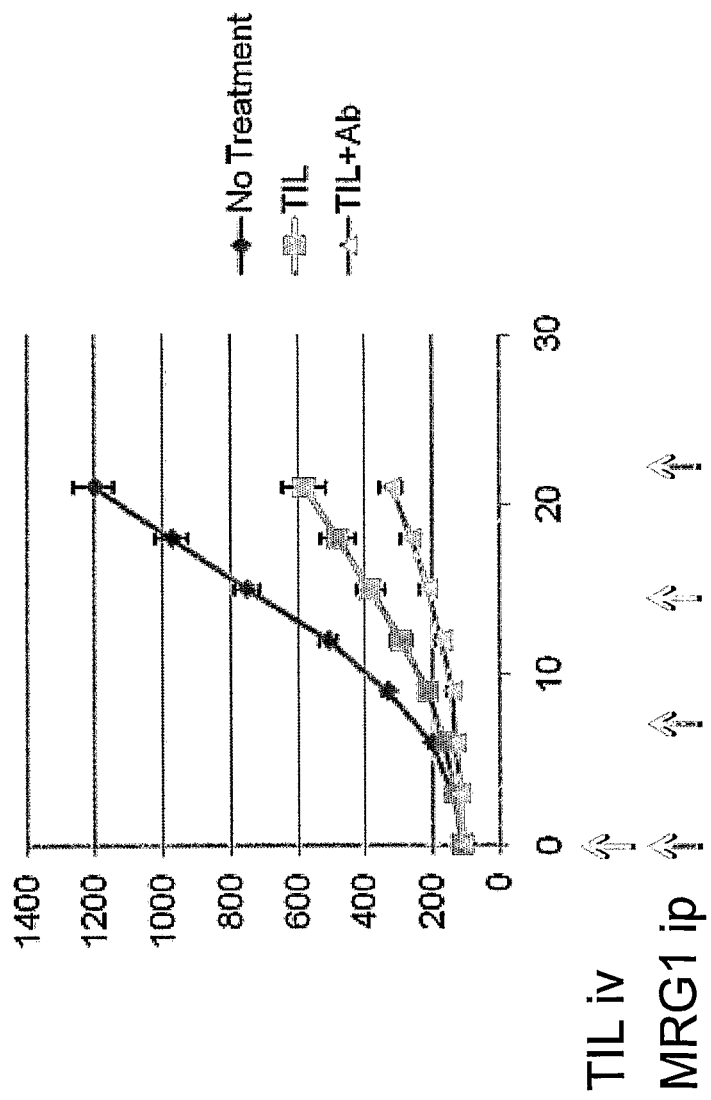
FIG. 7 depicts enhanced efficacy in inhibition of tumor growth by a combination of MRG1 with intravenous administration of human reactive TIL as compared to intravenous TIL only.

Simulation of anti-melanoma immune response was performed by a single intravenous injection of reactive human anti-melanoma lymphocytes, which inhibited tumor growth (FIG. 7). This effect was significantly enhanced by intraperitoneal MRG1 injections once a week.

Example 6

MRG1 is Superior to Previously Described Anti-CEACAM1 Antibodies

Materials and Experimental Procedures
Antibody screening by ELISA

CEACAM1 blocking activity was tested using a BW functional system as described in detail in Example 3, hereinabove.

100,000 BW/CEACAM1-zeta cells were pre-incubated with 15 ng/ml MRG1 mAb, 2600 ng/ml Kat4c mAb or 600ng/ml rabbit polyclonal anti-CEACAM antibody. Following one hour incubation on ice, 50,000 721.221/CEACAM1 cells were added and the secretion of mouse IL-2 was measured by sandwich ELISA (R&D Systems).

RESULTS

Figure 8:
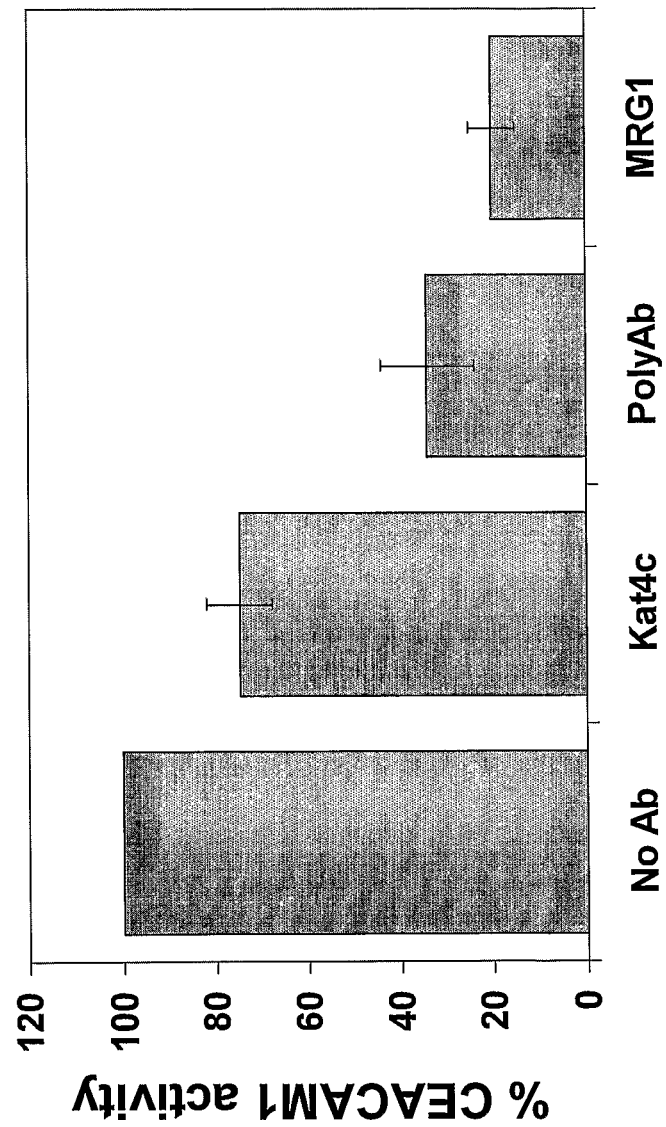
FIG. 8 depicts the superior effect of MRG1 mAb over previously described anti-CEACAM1 monoclonal antibodies, as well as commercially available rabbit polyclonal antibody targeting human CEACAM1 (DAKO, Glostrup Denmark), as determined by functional blocking assay. Various anti-CEACAM1 antibodies were tested for blocking of CEACAM1 activity, as reported by mIL-2 secretion. 100% was defined as activity in the absence of any antibody. The results of one representative experiment out of three are presented, each performed in triplicates.

As depicted in Example 3, hereinabove, the inventors demonstrated a nearly complete blocking of CEACAM1 activity using 15 ng/ml MRG1 mAb. In contrast, the anti-CEACAM1 monoclonal antibody Kat4c was able to yield a minor blocking effect only when 200-fold higher concentrations were tested and the polyclonal rabbit anti-CEACAM antibody yielded a similar inhibitory effect with 40-fold higher concentration (2600 ng/ml and 600ng/ml, respectively, FIG. 8).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A hybridoma cell which has been deposited under ATCC Accession Number PTA-9974.

2. An isolated antibody or antibody fragment that recognizes CEACAM1, and that comprises the same heavy chain variable region CDR1, CDR2 and CDR3 sequences, the same light chain variable region CDR1, CDR2 and CDR3 sequences, and the same orientation as the CDRs of the antibody produced from a hybridoma cell which has been deposited under ATCC Accession Number PTA-9974.

3. The isolated antibody or antibody fragment of claim 2 attached to a cytotoxic moiety.

4. The isolated antibody or antibody fragment of claim 3, wherein said cytotoxic moiety comprises a cytotoxin, a chemokine, a chemotherapy, a pro-apoptotic, an interferon, a radioactive moiety, or combinations thereof.

5. The isolated antibody or antibody fragment of claim 2 attached to an identifiable moiety.

6. A method of immunomodulation, the method comprising contacting a CEACAM1-expressing lymphocyte with the antibody or antibody fragment of claim 2.

7. A method of inhibiting migration or proliferation of a CEACAM1 expressing tumor cell, the method comprising contacting the CEACAM1 expressing tumor cell with the antibody or antibody fragment of claim 2, thereby inhibiting migration or proliferation of a CEACAM1 expressing tumor cell.

8. A method for determining the expression of CEACAM1, the method comprising contacting a biological sample with the antibody or antibody fragment of claim 2, and measuring the level of immune complex formation.

9. A method of treating a CEACAM1-expressing cancer, the method comprising administering to a subject in need thereof a therapeutically effective amount of the antibody or antibody fragment of claim 2, thereby treating the cancer in the subject.

10. The method of claim 9, further comprising administering to the subject lymphocytes.

11. The method of claim 10, wherein said lymphocytes comprise T cells or NK cells.

12. A method of inhibiting CEACAM1 homotypic or heterotypic protein-protein interaction, the method comprising contacting a CEACAM1-expressing lymphocyte with the antibody or antibody fragment of claim 2, thereby inhibiting CEACAM1 homotypic or heterotypic protein-protein interaction.

13. The method of claim 6, wherein said CEACAM1-expressing lymphocyte is a Tumor Infiltrating Lymphocyte or NK cell.

14. The method of claim 6, wherein said CEACAM1-expressing lymphocyte is a cytotoxic T cell.

15. The method of claim 7, wherein said tumor cell comprises a melanoma tumor cell.

16. A pharmaceutical composition comprising as an active ingredient the antibody or antibody fragment of claim 2.

17. The isolated antibody or antibody fragment according to claim 2 wherein the antibody or antibody fragment is selective to humand CEACAM1.

18. The isolated antibody or antibody fragment according to claim 2 produced from the hybridoma cell which has been deposited under ATCC Accession Number PTA-9974.

* * * * *

UNITED STATES PATENT AND TRADEMARK OFFICE
Certificate

Patent No. 8,598,322 B2                                                          Patented: December 3, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gal Markel, Tel Aviv (IL); Rona Ortenberg, Tel Aviv (IL); and Jacob Schachter, Givatayim (IL).

Signed and Sealed this First Day of April 2014.

RAM R. SHUKLA
*Supervisory Patent Examiner*
Art Unit 1643
Technology Center 1600

UNITED STATES PATENT AND TRADEMARK OFFICE
CERTIFICATE OF CORRECTION

PATENT NO. : 8,598,322 B2
APPLICATION NO. : 13/318266
DATED : December 3, 2013
INVENTOR(S) : Markel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 23 days.

Signed and Sealed this
Twenty-second Day of September, 2015

Michelle K. Lee
*Director of the United States Patent and Trademark Office*